United States Patent

Harnisch et al.

[11] Patent Number: 4,927,729
[45] Date of Patent: * May 22, 1990

[54] COLORLESS SALTS OF HETEROPOLYACIDS AS CHARGE CONTROL SUBSTANCES IN TONERS

[75] Inventors: Horst Harnisch, Much; Roderich Raue, Leverkusen, both of Fed. Rep. of Germany

[73] Assignee: Bayer Aktiengesellschaft, Leverkusen, Fed. Rep. of Germany

[*] Notice: The portion of the term of this patent subsequent to Mar. 14, 2006 has been disclaimed.

[21] Appl. No.: 266,554

[22] Filed: Nov. 3, 1988

[30] Foreign Application Priority Data

Nov. 17, 1987 [DE] Fed. Rep. of Germany ....... 3738948

[51] Int. Cl.$^5$ .................. G03G 9/08; C07F 5/06; C07F 7/02; C07F 11/00
[52] U.S. Cl. .................... 430/110; 544/225; 546/10; 548/404
[58] Field of Search ............... 430/110; 544/225; 546/10; 548/404

[56] References Cited

U.S. PATENT DOCUMENTS

| | | | |
|---|---|---|---|
| 4,493,883 | 1/1985 | Gruber et al. | 430/110 |
| 4,683,188 | 7/1987 | Suzuki et al. | 430/110 |
| 4,812,379 | 3/1989 | Harnisch et al. | 430/110 |

Primary Examiner—Roland E. Martin
Attorney, Agent, or Firm—Sprung Horn Kramer & Woods

[57] ABSTRACT

Heteropolyacid salts of the formula

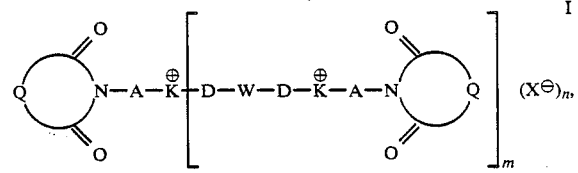

in which Q stands for 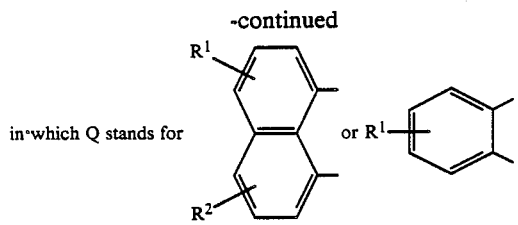

$R^1$ and $R^2$ independently of one another stand for hydrogen, chlorine, bromine, hydroxyl, $C_1$- to $C_4$-alkoxy, nitro or carboxyl,
A stand for $C_1$- to $C_5$-alkylene or —$C_6H_4$—$CH_2$— (m- or p-),
m stands for 0 or 1,
n stands for 1 or 2,
$K^\oplus$ stands for

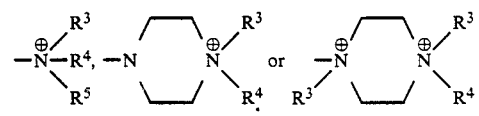

$R^3$ stands for $C_1$- to $C_{24}$-alkyl, carbamoyl-$C_1$- to $C_2$-alkyl, $C_1$- to $C_4$-alkoxycarbonyl-$C_1$- to $C_2$-alkyl, benzyl, cyclohexyl or allyl,
$R^4$ stands for $C_1$- to $C_4$-alkyl or a single bond linked to D,
$R^5$ stands for $C_1$- to $C_4$-alkyl,
D stands for —$CH_2$—, —$CH_2$—CO—, —$CH_2$—CO—NH— or —$CH_2$—CO—NH—$CH_2$—,
W stands for

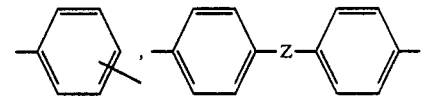

CO or for single bond,
Z stands for —$CH_2$—,

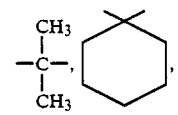

—O—, —S—, —$SO_2$— or a single bond and
$X^\ominus$ stands for an anion of a heteropolyacid based on tungsten and/or molybdenum containing phosphorus, silicon, vanadium, cobalt, nickel, manganese, chromium and/or aluminum, are used as additives for reinforcing the positive charge in electrographic toners.

7 Claims, No Drawings

COLORLESS SALTS OF HETEROPOLYACIDS AS CHARGE CONTROL SUBSTANCES IN TONERS

The invention relates to heteropolyacid salts of the formula

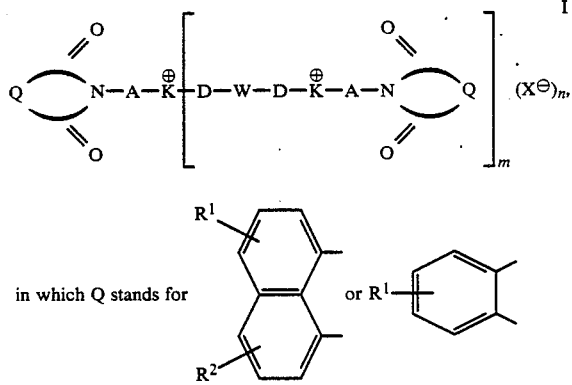

in which Q stands for

R$^1$ and R$^2$ independently of one another stand for hydrogen, chlorine, bromine, hydroxyl, C$_1$- to C$_4$-alkoxy, nitro or carboxyl,
A stands for C$_1$- to C$_5$-alkylene or —C$_6$H$_4$—CH$_2$— (m- or p-),
m stands for 0 or 1,
n stands for 1 or 2,
K$^\oplus$ stands for

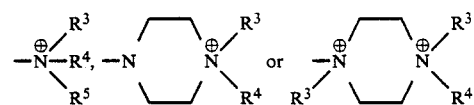

R$^3$ stands for C$_1$- to C$_{24}$-alkyl, carbamoyl-C$_1$- to C$_2$-alkyl, C$_1$- to C$_4$-alkoxycarbonyl-C$_1$- to C$_2$-alkyl, benzyl, cyclohexyl or allyl,
R$^4$ stands for C$_1$- to C$_4$-alkyl or a single bond linked to D,
R$^5$ stands for C$_1$- to C$_4$-alkyl,
D stands for —CH$_2$—, —CH$_2$—CO—, —CH$_2$—CO—NH— or —CH$_2$—CO—NH—CH$_2$—,
W stands for

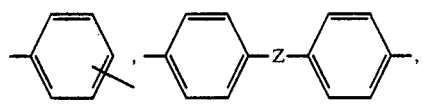

CO or a single bond,
Z stands for —CH$_2$—,

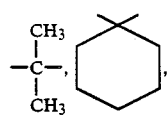

—O—, —S—, —SO$_2$— or a single bond and
X$^\ominus$ stands for an anion of a heteropolyacid based on tungsten and/or molybdenum containing phosphorus, silicon, vanadium, cobalt, nickel, manganese, chromium and/or aluminium. Preferably, R$^1$ and R$^2$ denote hydrogen.

C$_1$- to C$_5$-alkylene radicals A can be straightchain or branched. Of these, C$_2$-C$_5$-alkylene radicals and, in particular, the n-propylene radical are preferred.
Preferred alkyl radicals R$^3$ are C$_1$- to C$_{16}$-alkyl radicals.
Preferably, X$^\ominus$ stands for the anion of a heteropolyacid based on tungsten and/or molybdenum containing phosphorus or silicon.
The salts of the formula I are almost colourless and virtually insoluble in water. Their solubility in water at room temperature is preferably less than 0.1% by weight.
The invention further relates to toners for developing latent electrostatic images in electrostatic recording and printing processes containing as charge control substance a compound of the formula I.
Preferred compounds of the formula I correspond to the formula

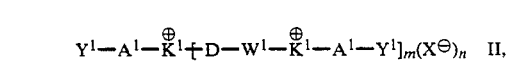

in which

Y$^1$ stands for

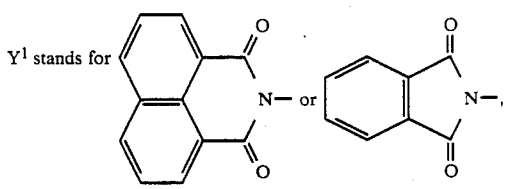

A$^1$ stands for C$_2$-C$_5$-alkylene,
K$^{\oplus 1}$ stands for

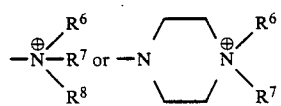

R$^6$ stands for C$_1$-C$_{16}$-alkyl, carbamoylmethyl or benzyl,
R$^7$ stands for methyl or ethyl or a single bond linked to D,
R$^8$ stands for methyl or ethyl,
W$^1$ stands for

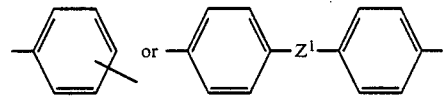

Z$^1$ stands for —CH$_2$—,

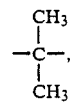

—O— or —SO$_2$— and
X$^\ominus$ stands for the anion of a heteropolyacid based on tungsten and/or molybdenum containing phosphorus or silicon and D, m and n have the same meaning as in formula I.
Of particular industrial importance are those compounds of the formula I in which
X$^\ominus$ stands for the phosphotungstomolybdate anion.

The compounds of the formula I can be prepared by precipitation from aqueous solutions of the colourless cationic substances described in German Offenlegungsschrift No. 3,604,827, European Patent No. 233,544 and U.S. Pat. No. 4,493,883 with a heteropolyacid of the formula

in which $X^\ominus$ has the abovementioned meaning, in the pH range from 2–4 and by isolation of the precipition product of the formula I.

Charge-reinforcing, colourless additives for electrophotographic toners—also colourless charge control substances—are already known. They are described in the abovementioned published specifications and patents.

Latent electrostatic recorded images are developed by depositing the toner inductively on the electrostatic image. The charge control substances reinforce the cationic charge of the toner. As a result, the image is reinforced and has sharper contours.

The resins contained in the toners are known. They are thermoplastic and have a softening temperature between 50° and 130° C., preferably between 65° and 115° C. Examples of such resins include polystyrene, copolymers of styrene with an acrylate or methacrylate, copolymers of styrene with butadiene and/or acrylonitrile, polyacrylates and polymethacrylates, copolymers of an acrylate or methacrylate with vinyl chloride or vinyl acetate, polyvinyl chloride, copolymers of vinyl chloride with vinylidene chloride, copolymers of vinyl chloride with vinyl acetate, polyester resins (U.S. Pat. No. 3,590,000), epoxy resins, polyamides and polyurethanes.

In addition to the compounds I and the thermoplastic resins, the toners according to the invention contain known amounts of dye materials and magnetically attractable material. The dye material can consist of an organic dyestuff such as nigrosine, aniline blue, 2,9-dimethylquinacridone, C.I. Disperse Red 15 (=C.I. 60,710), C.I. Solvent Red 19 (=C.I. 26,050), C.I. Pigment Blue 15 (=C.I. 74,160), C.I. Pigment Blue 22 (=C.I. 69,810) and C.I. Solvent Yellow 16 (=C.I. 12,700), or of an inorganic pigment such as soot, red lead, yellow lead oxide or chromium yellow. In general, the amount of the dye material present in the toners does not exceed about 15% by weight.

The magnetically attractable material can consist, for example, of iron, nickel, chromium oxide, iron oxide or a ferrite of the general formula $MFe_2O_4$ in which M represents a divalent metal such as iron, cobalt, zinc, nickel or manganese.

The preparation of the toners containing the compounds I is carried out by conventional processes, for example by mixing the components in a kneader, followed by pulverizing or by melting the thermoplastic resin or a mixture of the thermoplastic resins followed by finely dividing one or more charge control substances of the formula I and the other additives, if they are used, in the melted resin using known mixing and kneading machines for this purpose, followed by cooling the melt to give a solid mass and finally grinding this solid mass to give particles of the desired particle size. It is also possible to suspend the thermoplastic resin and the compound I in a common solvent and to incorporate the other additives in the suspension. In this form, the suspension can be used as liquid toner. However, it is also possible to spray dry the liquid in a manner known per se or to evaporate the solvent(s) and to grind the solid residue to give particles of the desired particle size.

According to a modification of this preparation process, the charge control substance of the formula I is not dissolved but finely dispersed in the solution of the thermoplastic resin.

The toner formulation thus obtained can be used in a xerographic recorded image process analogously to U.S. Pat. No. 4,265,990.

The charge control substances used must meet a variety of requirements.
1. Capability to develop the latent electrostatic image to give a strong visible image.
2. Easy distribution in the toner formulation and uniform distribution on the image surface to produce a uniform image free of defects and having sharp contours.
3. Insensitivity to moisture.
4. High thermal stability.
5. Resistance to the hot mixture consisting of lead oxide and a vinylidene fluoride/hexafluoropropylene copolymer resin (for example VITON®E-430 from Dupont) which makes it possible to fix the image by means of a hot roll. The coating material must not turn black due to decomposition products.
6. Non-toxic.

The charge control substances known from the above-mentioned published patents and specifications do not meet all of these requirements.

Surprisingly, it has now been found that the substances of the formula I in comparison with the hitherto known cationic compounds mentioned have, in addition to an increase in the depth of shade of the developed image and an improvement in the image sharpness, in particular a lower sensitivity to high humidity and a higher service life of the toner (more than 50,000 copies).

Particularly valuable are the phosphotungstomolybdates of the formula I.

EXAMPLE 1

N-(3-Naphthalimido-N'-propyl)-N,N,N-trimethylammonium phosphotungstomolybdate (a) Preparation of the phosphotungstomolybdate solution:

1290 g of water are initially introduced into a 2 l stirring apparatus equipped with reflux condenser and thermometer and 8.5 g of sodium hydroxide (0.2 mol) are added. The solution is heated to 90° C. 461.4 g of ammonium tungstate solution (50% of $WO_3$,=230.7 g, 100% strength, =1 mol), 28.5 g of molybdenum(VI) oxide (about 0.2 mol), 35.7 g of disodium hydrogenphosphate dihydrate, 27.9 g of crude hydrochloric acid (32% strength, =0.24 mol) and 53.6 g of sodium bisulphite solution 40% strength (0.2 mol) are then added in the sequence given and the solution is heated to boiling for 30 minutes (about 102° C.), cooled to 30° C. and the pH is adjusted to 4 with about 6.2 ml of hydrochloric acid (about 32% strength).

(b) Preparation of the solution to be precipitated:

3500 g of water are initially introduced into a 6 l stirring apparatus equipped with thermometer, dropping funnel and reflux condenser, 234 g of N-(3-naphthalimido-N'-propyl)-N,N,N-trimethylammonium toluenesulphonate (0.5 mol, prepared according to German Offenlegungsschrift No. 3,604,827, Example 22) are added with stirring and the mixture is heated to 50° C. to give a clear solution. The pH is then adjusted to 2 by dropwise addition of about 9 ml of hydrochloric acid.

(c) Precipitation:

1600 ml of the solution prepared in (a) are run into the solution prepared in (b) at 50°–55° C. over a period of 30–60 minutes with stirring. The reaction product crystallizes and the pH rises to >4. By dropwise addition of about 5.7 ml of hydrochloric acid, the pH is adjusted to 3.3 and stirring of the suspension is continued for 30 minutes at 50°–55° C. The crystalline precipitate is filtered off with suction at 50°–55° C., washed with a total of 5000 ml of water in 5 portions and dried in vacuo at 80° C. Yield: 388 g of the phosphotungstomolybdate mentioned in the title.

(d) Preparation of the toner:

100 g of styrene/n-butyl methacrylate copolymer (molecular weight: 50,000) and 5 g of the abovementioned phosphotungstomolybdate are evenly mixed in a kneader. After cooling, the resin is powdered in a jet mill to a mean grain fineness of 12μ. 5 g of this toner powder are charged by rotation with 95 g of a carrier material consisting of iron coated with a polymer and the charge is determined by the blow-off method. It amounts to 11.2 μC/g and is still as high as ever after 50,000 copies.

EXAMPLE 2

N-(3-Phthalimido-N'-propyl)-N,N,N-trimethylammonium phosphotungstomolybdate

Example 1 is repeated except that instead of the naphthalimido compound an equivalent amount of N-(3-phthalimido-N'-propyl)-N,N,N-trimethylammonium methosulphate (prepared according to U.S. Pat. No. 4,493,883, Example 1) is used.

This gives 319 g of the abovementioned phosphotungstomolybdate. After incorporation in the toner mixture mentioned in Example 1 (instead of the charge control substance used there), a positive charging of 13.0 μC/g is obtained.

EXAMPLE 3

N-(3-Naphthalimido-N'-propyl)-N,N,N-trimethylammonium silicomolybdate (a) Preparation of the complex solution as the precipitant 82.5 g of sodium molybdate×2 H$_2$O and 9.9 g of sodium metasilicate×5H$_2$O are added to 900 ml of water at 30° C. and the mixture is stirred for 30 minutes at 30° C. 0.9 g of sodium dichromate is then added to the solution and 60 ml of concentrated hydrochloric acid is added dropwise bringing the pH to 2.5–2.6. The solution is stirred for 15 minutes at 30° C. and the pH mentioned, brought to a volume of 1575 ml by adding water, heated to 50° C. and stirring is continued at this temperature for 10 minutes.

(b) Preparation of the ROSIN solution 2 l of water at 50° C. are initially introduced. 123.7 mg of NALCO-71-D5, 343 mg of AVITEX ML, 16.1 ml of glacial acetic acid and 46.8 g of N-(3-naphthalimido-N'-propyl)-N,N,N-trimethylammonium tosylate (0.1 mol) are added. The mixture is stirred for 5 minutes at 50° C. giving a cloudy solution. 40.3 g of ROSIN amine D acetate are added to the mixture at 50° C., which is stirred for a short time and brought to a volume of 2.6 ml with water.

(c) Precipitation 2600 ml of ROSIN amine solution, the preparation of which has been described in (b), are heated to 50° C., and 1525 ml of complex solution at 50° C., the preparation of which has been described in (a), are added dropwise. Excess complex solution in the suspension is detected using 0.1% strength quinine×HCl×2H$_2$O solution. To this effect, about 5 ml of the suspension are filtered and about 4 ml of quinine solution are added to the filtrate, excess complex solution being indicated by cloudiness in the form of flocs.

After the equivalence point is reached, the suspension is filtered off at 50° C., the precipitate is washed with 1 l of warm water at 50° C. and dried in vacuo at 60° C. Yield: 96.5 g of the silicomolybdate mentioned in the title.

Incorporation in the toner mixture mentioned in Example 1 (instead of the charge control substance used there) gives a positive charging of 7.8 μC/g.

The examples which follow can be prepared analogously, and—incorporated in a toner mixture according to Example 1(d)—have the following triboelectric chargings:

EXAMPLE 4

N-(3-Phthalimido-N'-propyl)-N,N,N-trimethylammonium silicomolybdate; positive charging: 3.6 μC/g.

EXAMPLE 5

N-(3-Naphthalimido-N'-propyl)-N,N-dimethyl-N-hexadecylammonium silicomolybdate, positive charging: 3.7 μC/g.

EXAMPLE 6

N-(3-Naphthalimido-N'-propyl)-N,N-dimethyl-N-octadecylammonium silicomolybdate

EXAMPLE 7

N-(3-Phthalimido-N'-propyl)-N,N-dimethyl-N-octadecylammonium silicomolybdate

EXAMPLE 8

N-(3-Naphthalimido-N'-propyl)-N,N-dimethyl-N-hexadecylammonium phosphotungstomolybdate A solution of 274 g (0.47 mol) of N-(3-naphthalimido-N'-propyl)-N,N-dimethyl-N-hexadecylammonium bromide (EP No. 233,544) in 1 l of isopropanol is run into a phosphotungstomolybdate solution prepared according to Example 1(a) with vigorous stirring at 50°–55° C., which leads to the precipitation of the corresponding phosphotungstomolybdate. The suspension is heated to 70°–75° C. for 15 minutes and then cooled. The crystalline precipitate is filtered off with suction, washed with water and dried in vacuo at 80° C. This gives 430 g of the phosphotungstomolybdate mentioned in the title.

Positive charging: 17.1 μC/g.

After 4 days in 65% humidity (20° C.), the positive charging is still 13.8 μC/g.

The examples which follow are prepared analogously to Example 8:

EXAMPLE 9

N-(3-Phthalimido-N'-propyl)-N,N-dimethyl-N-hexadecylammonium phosphotungstomolybdate

EXAMPLE 10

N-(3-Naphthalimido-N'-propyl)-N,N-dimethyl-N-octadecylammonium phosphotungstomolybdate

EXAMPLE 11

N-(3-Phthalimido-N'-propyl)-N,N-dimethyl-N-octadecylammonium phosphotungstomolybdate.

Formula $$Y\underset{O}{\overset{O}{\diagdown}}N-(CH_2)_3-\underset{CH_3}{\overset{CH_3}{\underset{|}{N^{\oplus}}}}-R \quad X^{\ominus}$$

| Example | Y | R | $X^{\ominus}$ |
|---|---|---|---|
| 1 | naphthalene | $CH_3$ | Phosphotungstomolybdate |
| 2 | benzene | " | " |
| 3 | naphthalene | " | Silicomolybdate |
| 4 | benzene | " | " |
| 5 | naphthalene | $CH_3-(CH_2)_{15}-$ | " |

-continued

Formula $$Y\underset{O}{\overset{O}{\diagdown}}N-(CH_2)_3-\underset{CH_3}{\overset{CH_3}{\underset{|}{N^{\oplus}}}}-R \quad X^{\ominus}$$

| Example | Y | R | $X^{\ominus}$ |
|---|---|---|---|
| 6 | naphthalene | $CH_3-(CH_2)_{17}-$ | Silicomolybdate |
| 7 | benzene | " | " |
| 8 | naphthalene | $CH_3-(CH_2)_{15}-$ | Phosphotungstomolybdate |
| 9 | benzene | " | " |
| 10 | naphthalene | $CH_3-(CH_2)_{17}-$ | " |
| 11 | benzene | " | " |

EXAMPLE 12

Methylenebis[(phenylene-4-amidomethyl)-(3-naphthalimido-N'-propyl)-dimethylammonium]chloride phosphotungstomolybdate The preparation of the phosphotungstomolybdate solution is carried out as described in Example 1(d). This solution is slowly run into a solution of 458 g (0.5 mol) of methylenebis[(phenylene-4-amidomethyl)-(3-naphthalimido-N'-propyl)-dimethylammonium]dichloride (prepared according to German Offenlegungsschrift No. 3,604,827, Example (1) in 4.2 l of water and 3.3 ml of concentrated hydrochloric acid at 80°–90° C. The pH is kept constant at 3–4 by the dropwise addition of a further 25 ml of concentrated hydrochloric acid. Stirring of the suspension is then continued for another 30 minutes at 80° C., followed by cooling of the suspension. The crystalline precipitate is filtered off with suction, washed with 4 l of water and dried in vacuo at 80° C. This gives 697 g of the phosphotungstomolybdate mentioned in the title. Under the conditions described in Example 1(d), it shows a positive charging of 15.5 μC/g.

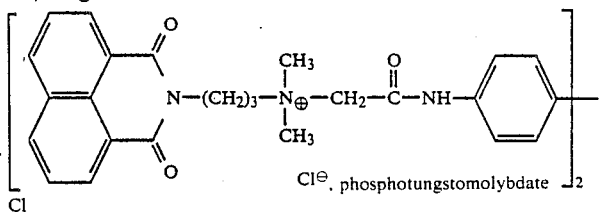

Compounds 13 to 21 which follow are prepared analogously to Example 12, Examples 22 to 23 which then follow are prepared analogously to Example 3:

| Example | Y | A | $\overset{\oplus}{K}$ | D | W | $X^{\ominus}$ |
|---|---|---|---|---|---|---|
| | | | | $\left[ \begin{array}{c} O \\ \parallel \\ N-A-\overset{\oplus}{K}-D- \\ \parallel \\ O \end{array} (Y) \right]_2 W\, Cl^{\ominus}, X^{\ominus}$ | | |
| 13 | benzene ring (ortho) | $-CH_2-\phantom{X}$(phenyl) | $\begin{array}{c}CH_3\\|\\-N^{\oplus}-\\|\\CH_3\end{array}$ | $-CH_2-CO-NH-$ | phenyl–$SO_2$–phenyl | Phosphotungstomolybdate |
| 14 | naphthalene | $\begin{array}{c}CH_3\\|\\-CH_2-C-CH_2-\\|\\CH_3\end{array}$ | " | " | phenyl–O–phenyl | " |
| 15 | " | $-CH_2-CH_2-$ | $\begin{array}{c}CH_2-CH_3\\|\\-N^{\oplus}-\\|\\CH_2-CH_3\end{array}$ | " | phenyl–S–phenyl | " |
| 16 | benzene ring (ortho) | $-CH_2-CH_2-CH_2-$ | $\begin{array}{c}CH_3\\|\\-N^{\oplus}-\\|\\CH_3\end{array}$ | " | $\begin{array}{c}CH_3\\|\\phenyl-C-phenyl\\|\\CH_3\end{array}$ | " |
| 17 | naphthalene | $-CH_2-\phantom{X}$(meta-phenyl) | $\begin{array}{c}CH_3\\|\\-N^{\oplus}-\\|\\CH_3\end{array}$ | $-CH_2-CO-NH-CH_2-$ | biphenyl | Phosphotungstomolybdate |

-continued $$\left[ Y \underset{O}{\overset{O}{\diagdown}} N - A - \overset{\oplus}{K} - D - \right]_2 W\ Cl^{\ominus}, X^{\ominus}$$

| Example | Y | A | K | D | W | $X^{\ominus}$ |
|---|---|---|---|---|---|---|
| 18 | " | —CH$_2$—CH$_2$— | ![N-methylpiperazinium] (1,4-dimethylpiperazinium) | —CH$_2$— | —CO— | " |
| 19 | " | —CH(CH$_3$)—(CH$_2$)$_3$— | (C$_2$H$_5$)$_2$$\overset{\oplus}{N}$(CH$_3$)— | " | para-phenylene | " |
| 20 | " | —CH$_2$—CH$_2$— | N-methylpiperidinium | —CH$_2$—CO— | 4,4'-oxydiphenylene | " |
| 21 | benzene-1,2-diyl | —CH$_2$—(p-C$_6$H$_4$)— | (CH$_3$)$_2$$\overset{\oplus}{N}$(CH$_3$)— | —CH$_2$—CO—NH— | 1,1-bis(4-phenyl)cyclohexane | " |
| 22 | naphthalene-1,8-diyl | —CH$_2$—CH$_2$—CH$_2$— | (CH$_3$)$_2$$\overset{\oplus}{N}$(CH$_3$)— | —CH$_2$—CO—NH— | 4,4'-methylenediphenylene | Silicomolybdate |
| 23 | benzene-1,2-diyl | " | " | " | " | " |

The compounds which follow are also prepared analogously to Example 12:

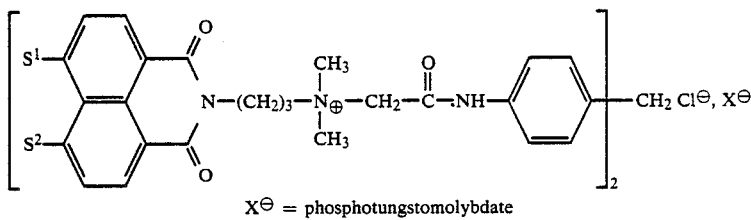

$X^\ominus$ = phosphotungstomolybdate

| Example | S¹ | S² |
|---|---|---|
| 24 | Cl | H |
| 25 | Cl | Cl |
| 26 | CH₃—O— | H |
| 27 | C₂H₅—O— | H |
| 28 | CH₃—O— | CH₃—O— |
| 29 | C₂H₅—O— | C₂H₅—O— |
| 30 | Br | H |
| 31 | Br | Br |
| 32 | COOH | H |
| 33 | COOH | COOH |

The compounds which follow are prepared analogously to Example 8:

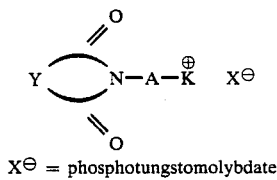

$X^\ominus$ = phosphotungstomolybdate

| Example | Y | A | $\overset{\oplus}{K}{}^1$ |
|---|---|---|---|
| 34 | ortho-disubstituted benzene | —CH₂—C(CH₃)(CH₃)—CH₂— | —⊕N(CH₃)(CH₃)—CH₂—phenyl |
| 35 | 1,8-naphthylene | —CH₂—CH₂— | —N(piperazinyl)⊕N(CH₃)(C₂H₅) |
| 36 | 4-chloro-1,5-naphthylene | —C₆H₄—CH₂— | —⊕N(CH₃)(CH₃)—CH₂—CONH₂ |
| 37 | 4,5-dichloro-1,8-naphthylene | —C₆H₄—CH₂— (meta) | —⊕N(CH₃)(CH₃)—C₄H₉(n) |

-continued $$Y\underset{O}{\overset{O}{\underset{\|}{\bigcap}}}N-A-\overset{\oplus}{K} \quad X^{\ominus}$$

$X^{\ominus}$ = phosphotungstomolybdate

| Example | Y | A | $\overset{\oplus}{K^1}$ |
|---|---|---|---|
| 38 | (o-dimethylbenzene ring) | —(CH$_2$)$_2$— | $-\overset{\oplus}{N}(CH_3)_2-CH_2-COOC_2H_5$ |
| 39 | (o-dimethylbenzene ring) | —(CH$_2$)$_3$— | $-\overset{\oplus}{N}(CH_3)_2-C_{10}H_{21}(n)$ |
| 40 | (bromo-naphthalene) | —(CH$_2$)$_2$— | piperazinium dimethyl (2 X$^{\ominus}$) |
| 41 | (CH$_3$O-naphthalene) | —(CH$_2$)$_3$— | $-\overset{\oplus}{N}(CH_3)_2-C_6H_{11}$ |
| 42 | (C$_2$H$_5$O, C$_2$H$_5$O-naphthalene) | —CH$_2$—C(CH$_3$)$_2$—CH$_2$— | $-\overset{\oplus}{N}(CH_3)_2-C_2H_5$ |
| 43 | (HOOC-naphthalene) | —(CH$_2$)$_3$— | $-\overset{\oplus}{N}(CH_3)_2-CH_2-CH=CH_2$ |

We claim:
1. Heteropolyacid salts of the formula

$$\left[Q\underset{O}{\overset{O}{\underset{\|}{\bigcap}}}N-A-\overset{\oplus}{K}-D-W-D-\overset{\oplus}{K}-A-N\underset{O}{\overset{O}{\underset{\|}{\bigcap}}}Q\right]_m (X^{\ominus})_n$$

in which Q is (naphthalene with R$^1$, R$^2$) or (benzene with R$^1$),

R$^1$ and R$^2$ independently of one another are hydrogen, chlorine, bromine, hydroxyl, C$_1$- to C$_4$-alkoxy, nitro or carboxyl,
A is C$_1$- to C$_5$-alkylene or —C$_6$H$_4$—CH$_2$— (m- or p-),
m is 0 or 1, n is 1 or 2,
K+ is

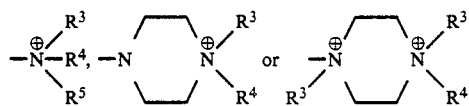

R³ is C₁- to C₂₄-alkyl, carbamoyl-C₁- to C₂-alkyl, C₁- to C₄-alkoxycarbonyl-C₁- to C₂-alkyl, benzyl, cyclohexyl or allyl,
R⁴ is C₁- to C₄-alkyl or a single bond linked to D,
R⁵ is C₁- to C₄-alkyl,
D is —CH₂—, —CH₂—CO—, —CH₂—CO—NH— or —CH₂—CO—NH—CH₂—,
W is

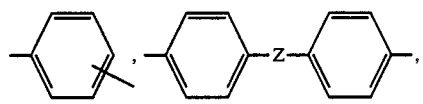

CO or a single bond,
Z is —CH₂—,

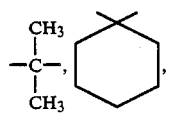

—O—, —S—, —SO₂— or a single bond and
X⊖ is an anion of a heteropolyacid based on tungsten and/or molybdenum containing phosphorus, silicon, vanadium, cobalt, nickel, manganese, chromium and/or aluminium.

2. Salts according to claim 1, in which X⊖ is the anion of a heteropolyacid based on tungsten and/or molybdenum containing phosphorus or silicon.

3. Salts of the formula

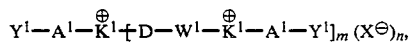

in which
Y¹ is

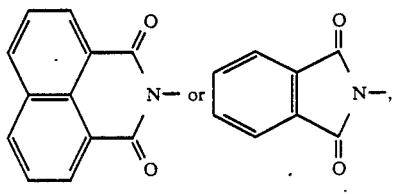

A¹ is C₂-C₅-alkylene,
K⊕¹ is

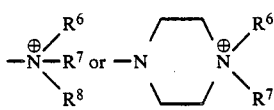

R⁶ is C₁-C₁₆-alkyl, carbamoylmethyl or benzyl,
R⁷ is methyl or ethyl or a single bond linked to D,
R⁸ is methyl or ethyl,
W¹ is

Z¹ is —CH₂—,

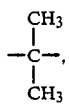

—O— or —SO₂— and
X⊖ is the anion of a heteropolyacid based on tungsten and/or molybdenum containing phosphorus or silicon and D, m and n have the same meaning as in claim 1.

4. Salts according to claim 1, in which X⊖ is the phosphotungstomolybdate anion.

5. Electrographic toners containing as the cationic charge-reinforcing additive a salt according to claim 1.

6. Electrographic toners according to claim 5, containing in addition to the cationic charge-reinforcing additive, resin and pigment particles.

7. A method of developing a latent electrostatic image comprising applying to said image a toner containing an additive reinforcing the positive charge according to claim 1.

* * * * *

UNITED STATES PATENT AND TRADEMARK OFFICE
CERTIFICATE OF CORRECTION

PATENT NO. : 4,927,729

DATED : May 22, 1990

INVENTOR(S) : Horst Harnisch, et al

It is certified that error appears in the above-identified patent and that said Letters Patent is hereby corrected as shown below:

Col. 18, line 25    After  delete "," and substitute --or--

Col. 18, line 25    Between structures, delete "Z" and substitute --$Z^1$--

Signed and Sealed this

Twenty-eighth Day of January, 1992

Attest:

HARRY F. MANBECK, JR.

Attesting Officer    Commissioner of Patents and Trademarks